United States Patent [19]

Nambu et al.

[11] 4,355,190

[45] Oct. 19, 1982

[54] PROCESS FOR RECOVERY OF RESORCINOL FROM AQUEOUS RESORCINOL SOLUTION CONTAINING HYDROQUINONE

[75] Inventors: Hirohiko Nambu; Fujihisa Matsunaga; Hiroaki Nakagawa, all of Iwakuni, Japan

[73] Assignee: Mitsui Petrochemical Industries, Ltd., Tokyo, Japan

[21] Appl. No.: 215,123

[22] Filed: Dec. 10, 1980

[30] Foreign Application Priority Data

Dec. 13, 1979 [JP] Japan ................................. 54-160878

[51] Int. Cl.³ ............................................. C07C 37/68
[52] U.S. Cl. .................................... 568/754; 568/750; 568/753; 568/768
[58] Field of Search ................ 568/754, 753, 750, 768

[56] References Cited

U.S. PATENT DOCUMENTS 2,006,589  7/1935  Henry .................................. 568/750
3,862,244  1/1975  Genod et al. ........................ 568/754
3,928,469  12/1975  Suda et al. .......................... 568/768
4,145,283  3/1979  Topp et al. ......................... 568/754

FOREIGN PATENT DOCUMENTS 2357844  6/1974  Fed. Rep. of Germany ...... 568/753
2357845  6/1974  Fed. Rep. of Germany ...... 568/768
40-4740  3/1965  Japan ................................. 568/754
46-18975  5/1971  Japan ................................. 568/754
775813  5/1957  United Kingdom ................ 568/754

*Primary Examiner*—Werren B. Lone
*Attorney, Agent, or Firm*—Sherman & Shalloway

[57] ABSTRACT

A process for recovery of resorcinol from an aqueous resorcinol solution containing hydroquinone which comprises oxidizing an aqueous resorcinol solution containing about 10 to about 60% by weight of resorcinol and up to about 1% by weight of hydroquinone with molecular oxygen at conditions of pH 6.5 to 9.5, followed by recovering resorcinol from the resultant oxidation product.

3 Claims, No Drawings

PROCESS FOR RECOVERY OF RESORCINOL FROM AQUEOUS RESORCINOL SOLUTION CONTAINING HYDROQUINONE

The present invention relates to a process for recovery of resorcinol to commercial advantage from an aqueous resorcinol solution containing hydroquinone, said hydroquinone being difficult to separate and remove from the end product resorcinol. According to the process of the present invention, by selectively oxidizing hydroquinone contained in the aqueous resorcinol solution, the hydroquinone is converted to a compound easy to separate from resorcinol and resorcinol not containing the hydroquinone or being markedly reduced in the hydroquinone impurity can be recovered from the oxidation product so obtained by such easy means as by distillation.

More particularly, the present invention relates to a process for recovery of resorcinol from an aqueous resorcinol solution containing hydroquinone which comprises oxidizing an aqueous resorcinol solution containing about 10 to about 60% by weight of resorcinol and up to about 1% by weight of hydroquinone with molecular oxygen at conditions of pH 6.5 to 9.5, followed by recovering resorcinol from the resultant oxidation product.

As one of processes for commercial production of resorcinol, there is known, for instance, a process for acid-cleavage of meta-diisopropylbenzene dihydroperoxide (hereinafter sometimes called m-DHP for short) obtained by oxidizing meta-diisopropylbenzene (hereinafter sometimes called m-DIPB for short) with air and it is commercially carried out. The m-DIPB can be formed by the reaction of benzene and/or cumene with propylene, for instance. Usually, the resulting reaction product is obtained as a mixture of ortho-, meta- and para-diisopropylbenzenes (o-, m- and p-DIPB's). m-DIPB can be used by separating and recovering from this mixture.

Due to difficulty in separation of m-DIPB and p-DIPB, however, in many cases, m-DIPB recovered contains a small amount of p-DIPB. The acid-cleavage product obtained by subjecting m-DHP obtained by oxidizing such m-DIPB containing p-DIPB with air to the known acid-cleavage reaction contains, besides m-DIPB, a small amount of hydroquinone formed by the acid-cleavage reaction of p-DIPB. Or in the case of employing the mode of practice that the production of resorcinol and production of hydroquinone are alternately conducted as the case may be by use of the same apparatus, such as conducting the production of resorcinol and then conducting the production of hydroquinone, in some cases, small amounts of hydroquinone may be mixed to the resorcinol manufacture system.

In the above-cited case, the acid-cleavage product of m-DHP containing para-diisopropylbenzene dihydroperoxide (hereinafter sometimes called p-DHP for short) becomes resorcinol containing hydroquinone. Such an acid-cleavage product is treated optionally by neutralization, extraction or the like by use of means known per se. for removal of acid catalyst used in the acid-cleavage, further, low boiling components, such as acetone, solvent used in the acid-cleavage reaction and so on, are removed by distillation and then it undergoes such known treatment as by distillation or by optional pyrolysis of high boiling components whereby crude resorcinol can be recovered.

However, the crude resorcinol derived from the acid-cleavage product of m-DHP containing p-DHP, viz., the resorcinol-containing distillation fraction, is accompanied with hydroquinone formed by the acid-cleavage reaction of p-DHP which is inseparable by the said distillation treatment and pyrolysis treatment. Such crude resorcinol can be recovered as crystallized high purity resorcinol freed from hydroquinone or markedly reduced in the hydroquinone content by the recrystallization method using aromatic hydrocarbons, such as benzene, toluene, xylene and cumene, by means known per se.

The mother liquor of recrystallization from which high purity resorcinol was recovered in this manner contains, besides hydroquinone, resorcinol in not negligible amounts. A method by which to advantageously remove resorcinol by way of easy means, avoiding the concomitant of hydroquinone, if any, will be helpful for the improvement of resorcinol yield in the process for the commercial production of resorcinol. The fact is, however, that recovery of resorcinol like that is overlooked due to difficulty lying in separation of resorcinol and hydroquinone.

The said loss of resorcinol could be avoided, for instance, by contacting the mother liquor of recrystallization with water to extract and move resorcinol and hydroquinone to aqueous phase and separating aqueous phase and oil phase, reusing the said oil phase containing aromatic hydrocarbons in the said recrystallization step and recyclically using the said aqueous phase in the said neutralization treatment and/or extraction treatment step for removal of acid catalyst from the acid-cleavage product or reusing, for instance, in the step of removing acetone or in the step of recovering the solvent used in the acid-cleavage whereby recycling the resorcinol being otherwise lost as the above in the resorcinol manufacture system.

By such means, however, hydroquinone as well is recycled in the resorcinol manufacture system, with the result that hydroquinone formed by acid-cleavage accumulates secondarily in the resorcinol manufacture system, causing, in turn, the inconvenience that the hydroquinone is mixed to the resorcinol crystals obtained from recrystallization.

The present inventors studied with a view to providing a means by which to remove hydroquinone alone from the aforesaid resorcinol manufacture system effectively as well as with commercial ease without causing such inconveniences and by which to advantageously avoid the aforesaid loss of resorcinol, in consequence of which it was found that by subjecting the aqueous resorcinol solution containing resorcinol and small amounts of hydroquinone to oxidation treatment, the hydroquinone contained in the said aqueous solution could be converted to a compound capable of easy separation from resorcinol by easy means such as by distillation.

This means was found to be favorably applicable to the aqueous resorcinol solution containing resorcinol and small amounts of hydroquinone obtained by recovering resorcinol by the recrystallization method from the resorcinol-containing distillation fraction derived from the said acid-cleavage product of m-DHP containing p-DHP and extracting resorcinol with water from the remaining mother liquor and likewise applicable to optional subject matters from which resorcinol is intended to be recovered by selectively removing hydroquinone from optional aqueous resorcinol solutions containing resorcinol and small amounts of hydroquinone.

Studies made by the instant inventors showed that the said oxidation treatment could be advantageously effected particularly preferably by oxidizing the aqueous resorcinol solution containing about 10 to about 60% by weight of resorcinol and up to about 1% by weight of hydroquinone with molecular oxygen at conditions of pH 6.5 to 9.5.

Therefore, the purpose of the present invention is to provide a process for recovery of resorcinol to commercial advantage from an aqueous resorcinol solution containing resorcinol and small amounts of hydroquinone.

The above purpose and many other purposes and merits of the present invention will be more cleared up from explanations given below.

The present invention provides a process for recovery of resorcinol from an aqueous resorcinol solution containing hydroquinone which comprises oxidizing an aqueous resorcinol solution containing about 10 to about 60% by weight of resorcinol and up to about 1% by weight of hydroquinone with molecular oxygen at conditions of pH 6.5 to 9.5, preferably about 7 to about 9, followed by recovering resorcinol from the resultant oxidation product.

It is important to set pH conditions as falling in the said range of pH values. If it is as low as less than pH 6.5, the rate at which hydroquinone is converted to a compound easy to separate from resorcinol by selective oxidation is too slow and it is not suited to commercial practice. If it is as high as in excess of pH 9.5, resorcinol as well is liable to undergo the oxidation and the oxidation of resorcinol caused to take place is not negligible. Consequently, the oxidation with molecular oxygen should be conducted at such conditions as to meet the said pH conditions.

For control over pH it can be effected by the addition of an appropriate aqueous solution of a watersoluble basic compound to the aqueous resorcinol solution containing resorcinol and hydroquinone. Examples of such water-soluble basic compounds include hydroxides, carbonates and the like of alkali metals or alkaline earth metals, such as sodium hydroxide, potassium hydroxide, calcium hydroxide, sodium carbonate, potassium carbonate and so forth.

For the oxidation with molecular oxygen there can be cited molecular oxygen or molecular oxygen-containing gases, such as oxygen, air and their mixture and mixtures of oxygen with inert gases, such as nitrogen, argon, helium and so on, and it is air that is commercially advantageously used. The oxidation reaction can be conducted by blowing molecular oxygen as cited above in the aqueous resorcinol solution containing hydroquinone. The reaction temperatures may be temperatures falling in the range of about 50° to about 100° C., preferably temperatures in the order of about 60° to about 90° C. If the reaction temperature is as low as to deviate from the above cited temperature range, the oxidation reaction rate goes lower, whereas if the reaction temperature is as high as to deviate from the said range, resorcinol as well is liable to undergo the oxidation. Consequently, those temperatures falling in the said cited range should optionally be chosen. The reaction time can suitably vary according to pH conditions, temperature conditions and so forth, but the oxidation treatment time such as about 0.1 to about 6 hours can be cited.

The structure of the compound to which the hydroquinone contained in the oxidation reaction system is converted by the said oxidation with molecular oxygen still remains unclarified, but probably it is converted to a compound with higher boiling points than that of resorcinol which is surmised to be a mixture of a plurality of compounds and can be separated and removed as the bottom component by distilling off and recovering resorcinol by distillation means, for instance. As the hereinafter-described Table 1 indicates, according to the process of the present invention, as the said oxidation goes on, the amount of hydroquinone contained in the oxidation reaction system is selectively lowered considerably rapidly and the intended resorcinol slightly falls off.

The process of the present invention is favorably applicable to treatment of aqueous resorcinol solution containing about 10 to about 60% by weight of resorcinol and up to about 1% by weight, such as about 0.0001 to about 1% by weight, of hydroquinone.

As one example for preferred modes of practice of the process of the present invention there can be cited a mode of practice of oxidizing with molecular oxygen an aqueous resorcinol solution containing about 10 to about 60% by weight of resorcinol and up to about 1% by weight of hydroquinone as aqueous phase obtained by recovering resorcinol by the recrystallization method from a resorcinol-containing distillation fraction derived from an acid-cleavage product of m-DHP containing p-DHP and extracting resorcinol with water from the remaining mother liquor, recycling the oxidation product so formed to a distillation step or pyrolysis step designed for collection of the said resorcinol-containing distillation fraction and removing the oxidation product of hydroquinone as a bottom component out of the system whereby recovering resorcinol.

The process of recovering resorcinol by the recrystallization method from the resorcinol-containing distillation fraction derived from the acid-cleavage product of m-DHP containing p-DHP is known in itself. Explanation will be given here of one example for the said modes of practice, including this known process.

The acid-cleavage reaction of m-DHP containing p-DHP can be conducted, for instance, by dissolving m-DHP containing p-DHP in dialkylketones or mixtures of dialkylketones and aromatic hydrocarbons and treating in the presence of an acid catalyst, such as sulfuric acid, phosphoric acid, perchloric acid or silica-alumina at temperatures of 20° to 120° C. for 1 minute to 3 hours.

For one thing, the resorcinol-containing distillation fraction can be obtained from the acid-cleavage product of m-DHP containing p-DHP obtained as the above as follows. The acid-cleavage product is neutralized by bringing into contact with alkali-containing aqueous solutions, such as caustic soda, sodium carbonate, potassium hydroxide and so on, or when using silica-alumina or the like as acid-cleavage catalyst, the acid cleavage catalyst is first removed by filtration, then acetone caused to occur by the acid cleavage and solvent of the acid-cleavage reaction are recovered on distillation and the residue containing resorcinol and small amounts of hydroquinone obtained is distilled at conditions of 150° to 300° C. under reduced pressure whereby there can be obtained the resorcinol-containing distillation fraction.

For one thing, recovery of resorcinol by the recrystallization method from the resorcinol-containing distillation fraction obtained as the above can be effected as follows. By the addition of aromatic hydrocarbons, such as benzene, toluene, xylene and cumene, in the amount, by weight, of 0.5 to 5 times as much the resorcinol-containing distillation fraction is dissolved by heating to make a homogeneous solution. After that, by cooling it gives a slurry containing resorcinol crystals. By centrifuging this slurry resorcinol can be obtained as crystals.

The mother liquor from which resorcinol was recovered as the above contains aromatic hydrocarbons used as the recrystallization solvent, resorcinol, hydroquinone and so forth. If this mother liquor is contacted with water, resorcinol and hydroquinone are extracted in aqueous phase. Extraction can be effected, for instance, by continuous extraction operation by which to countercurrently contact the mother liquor with extraction water, using the extraction water in the amount of 0.05 to 2 parts by weight based on the amount of the mother liquor.

The oil phase (aromatic hydrocarbon phase) obtained in such a manner can be reused in the said recrystallization step, for instance. On the other hand, the aqueous phase, as already mentioned, is oxidized with molecular oxygen according to the process of the present invention, the oxidation product so obtained is returned to the said step for the neutralization of the acid-cleavage product or step for the removal of acetone or step for the recovery by distillation of the solvent for the acid-cleavage reaction whereby resorcinol contained in the oxidate can be recovered.

Explanations will be given here in more detail of several modes of practice for the process of the present invention by way of Examples with addition of Comparative Examples.

EXAMPLES 1-4 AND COMPARATIVE EXAMPLES 1-3

Charged into an elongated reactor with an inner capacity of 300 ml, equipped with a hot water jacket, reflux condensor, stirrer and sparger was aqueous solution containing about 30% by weight of resorcinol and about 0.2% by weight of hydroquinone, which was obtained by contacting with water the mother liquor after resorcinol was recovered by the recrystallization method from the resorcinol-containing fraction derived from the acid-cleavage product of m-DHP containing p-DHP, followed by separating between oil and water. There was obtained 250 ml of aqueous solution held at pH indicated in the hereinafter-described Table 1 by adding sodium hydroxide. By blowing air in it at the rate of 30 1/hr the oxidation reaction was carried out with stirring at 80° C. Table 1 indicates reaction conditions and changes of concentrations of the respective components for reaction times.

TABLE 1

| | Molar ratio of amount of NaOH added to RS | pH | | Reaction time (minute) | | | | | | | | RS fraction of oxidate after oxidation for 90 minutes | |
|---|---|---|---|---|---|---|---|---|---|---|---|---|---|
| | | | | 0 | 10 | 20 | 30 | 60 | 90 | 110 | 150 | RS purity | RS recovery percent |
| Comparative Example 1 | 0 | 3.9 | RS (wt %) | 29.8 | — | — | 29.8 | 29.8 | 29.8 | 29.7 | 29.7 | 95.3 | 98.0 |
| | | | HQ (ppm) | 2440 | — | — | 2440 | 2420 | 2400 | 2380 | 2380 | | |
| Example 1 | 0.002 | 6.6 | RS (wt %) | 29.8 | — | — | 29.8 | 29.8 | 29.8 | 29.7 | 29.7 | 97.8 | 98.3 |
| | | | HQ (ppm) | 2440 | — | — | 1960 | 1710 | 1550 | 1480 | 1250 | | |
| Example 2 | 0.03 | 7.5 | RS (wt %) | 29.1 | — | 28.9 | 28.8 | 28.8 | 28.8 | — | — | 99.0 | 97.5 |
| | | | HQ (ppm) | 1790 | — | 500 | 310 | 50 | 0 | — | — | | |
| Example 3 | 0.07 | 7.9 | RS (wt %) | 29.1 | 28.4 | 28.3 | 28.3 | 28.2 | — | — | — | 99.0 | 96.0 |
| | | | HQ (ppm) | 1790 | 440 | 200 | 130 | 0 | — | — | — | | |
| Example 4 | 0.41 | 9.4 | RS (wt %) | 29.6 | 27.8 | 25.3 | 24.2 | 24.0 | 23.9 | — | — | 98.3 | 80.0 |
| | | | HQ (ppm) | 2300 | 1800 | 1210 | 760 | 350 | 120 | — | — | | |
| Comparative Example 2 | 0.56 | 10.0 | RS (wt %) | 29.1 | — | 21.6 | 19.1 | 18.2 | 15.4 | 13.4 | — | 95.6 | 51.8 |
| | | | HQ (ppm) | 2500 | — | 2500 | 2500 | 1470 | 450 | 0 | — | | |
| Comparative Example 3 | 0.57 | 10.7 | RS (wt %) | 28.6 | 26.2 | 23.8 | 20.5 | 17.7 | 12.8 | 10.2 | — | 95.1 | 43.4 |
| | | | HQ (ppm) | 2330 | 2160 | 1930 | 1820 | 1550 | 650 | 0 | — | | |

RS: Resorcinol,
HQ: Hydroquinone;
In the table, the horizontal line indicates no measurement was made.

EXAMPLES 5-7

Experiments were conducted in the same manner except that the reaction temperature was set as indicated in Table 2 with the pH of the aqueous solution held at 7.5 by the addition of sodium hydroxide. Table 2 indicates results.

TABLE 2

| | Reaction temperature °C. | | Reaction time (minute) | | | | | | |
|---|---|---|---|---|---|---|---|---|---|
| | | | 0 | 20 | 40 | 60 | 80 | 100 | 140 |
| Example 5 | 50 | RS (wt %) | 28.2 | 28.1 | 28.0 | 27.4 | 27.3 | 27.3 | 26.6 |
| | | HQ (ppm) | 2300 | 1650 | 1220 | 820 | 470 | 380 | 6 |
| Example 6 | 70 | RS (wt %) | 28.7 | 28.6 | 28.4 | 28.2 | 28.0 | — | — |
| | | HQ (ppm) | 2030 | 830 | 250 | 60 | 0 | — | — |
| Example 2 | 80 | RS (wt %) | 29.1 | 28.9 | 28.8 | 28.8 | 28.8 | — | — |
| | | HQ (ppm) | 1790 | 500 | 250 | 50 | 0 | — | — |
| Example 7 | 88 | RS (wt %) | 28.6 | 28.2 | 27.9 | 27.8 | — | — | — |
| | | HQ (ppm) | 1700 | 550 | 280 | 0 | — | — | — |

We claim:

1. A process for recovery of resorcinol from an aqueous resorcinol solution containing hydroquinone which comprises oxidizing an aqueous resorcinol solution containing about 10 to about 60% by weight of resorcinol and up to about 1% by weight of hydroquinone with molecular oxygen at conditions of pH 6.5 to 9.5, and a temperature of about 50° to about 100° C., followed by recovering resorcinol from the resultant oxidation product.

2. A process according to claim 1 in which the pH is set at about 7 to about 9.

3. A process according to claim 1 in which the aqueous resorcinol solution containing hydroquinone is an aqueous phase obtained by contacting with water a mother liquor after resorcinol was recovered by the recrystallization method from a resorcinol-containing distillation fraction derived from an acid-cleavage product of metadiisopropylbenzene dihydroperoxide containing paradiisopropylbenzene dihydroperoxide.

* * * * *